United States Patent
Reddy et al.

(10) Patent No.: US 10,336,703 B2
(45) Date of Patent: Jul. 2, 2019

(54) PROCESS FOR THE SYNTHESIS OF IVACAFTOR AND RELATED COMPOUNDS

(71) Applicant: Council of Scientific and Industrial Research, New Delhi (IN)

(72) Inventors: Dumbala Srinivasa Reddy, Pune (IN); Vasudevan Natarajan, Maharashtra (IN); Gorakhnath Rajaram Jachak, Maharashtra (IN)

(73) Assignee: Council of Scientific and Industrial Research, New Delhi (IN)

(*) Notice: Subject to any disclaimer, the term of this patent is extended or adjusted under 35 U.S.C. 154(b) by 0 days.

(21) Appl. No.: 15/573,438

(22) PCT Filed: May 12, 2016

(86) PCT No.: PCT/IN2016/050137
§ 371 (c)(1),
(2) Date: Nov. 10, 2017

(87) PCT Pub. No.: WO2016/181414
PCT Pub. Date: Nov. 17, 2016

(65) Prior Publication Data
US 2018/0127373 A1 May 10, 2018

(30) Foreign Application Priority Data
May 12, 2015 (IN) .......................... 1324/DEL/2015

(51) Int. Cl.
*C07D 215/56* (2006.01)
*A61K 31/47* (2006.01)
*C07B 33/00* (2006.01)
*C07C 227/06* (2006.01)

(52) U.S. Cl.
CPC ............ *C07D 215/56* (2013.01); *A61K 31/47* (2013.01); *C07B 33/00* (2013.01); *C07C 227/06* (2013.01)

(58) Field of Classification Search
CPC ...... C07D 215/56; C07B 33/00; A61K 31/47; C07C 227/06
See application file for complete search history.

(56) References Cited

U.S. PATENT DOCUMENTS

| | | | |
|---|---|---|---|
| 4,981,854 A | 1/1991 | Grohe et al. | |
| 7,402,674 B2 | 7/2008 | Defossa et al. | |
| 7,495,103 B2 | 2/2009 | Hadida-Ruah et al. | |
| 2010/0267768 A1 | 10/2010 | DeMattei et al. | |
| 2011/0064811 A1 | 3/2011 | Hurter et al. | |
| 2011/0230519 A1 | 9/2011 | Arekar et al. | |

FOREIGN PATENT DOCUMENTS

| | | |
|---|---|---|
| CN | 103044263 | 4/2013 |
| WO | WO-2007107545 | 9/2007 |
| WO | WO-2014125506 | 8/2014 |
| WO | WO-2016181414 | 11/2016 |

OTHER PUBLICATIONS

Vasudevan, Eur J Org Chem, 2015, 7433-7437. (Year: 2015).*
"International Application No. PCT/IN2016/050137, International Search Report and Written Opinion dated Aug. 18, 2016", (Aug. 18, 2016), 11 pgs.
"International Application No. PCT/IN2016/050137, Notification Concerning Filing of Amendments of the Claims (Article 19) mailed Oct. 19, 2016", (Oct. 19, 2016), 23 pgs.
Avila-Zárraga, José Gustavo, et al., "Supplementary Data New Heck Coupling Strategies for the Synthesis of Paullone and Dimethyl Paullone", (Jan. 1, 2006), pp. S1-S16, XP055294448, <URL:http://www.sciencedirect.com/science/MiamiMultiMediaURL/1-s2.0-S0040403906017473/1-s2.0-S0040403906017473-mmc1.doc/271373/html/S0040403906017473/2986918099169dbcb73339c88fc878ac/mmc1.doc>, (Jan. 1, 2006), 16 pgs.
Hadida, Sabine, et al., "Discovery of N-(2,4-Di-tert-butyl-5-hydroxyphenyl)-4-oxo-1,4-dihydroquinoline-3-carboxamide (VX-770, Ivacaftor), a Potent and Orally Bioavailable CFTR Potentiator", J. Med. Chem., 2014, 57 (23), pp. 9776-9795, (Nov. 4, 2014), 9776-9795.
Avila-Zárraga, José Gustavo, et al., "New Heck coupling strategies for the synthesis of paullone and dimethyl paullone", Tetrahedron Letters, vol. 47, Issue 45, Nov. 6, 2006, pp. 7987-7989, (Sep. 26, 2006), 7987-7989.
He, Yang, et al., "Expeditious Synthesis of Ivacaftor", Heterocycles, vol. 89, No. 4, 2014, pp. 1035-1040, (Mar. 6, 2014), 1035-1040.
Meinke, Peter T., et al., "Synthesis of Apicidin-Derived Quinolone Derivatives:? Parasite-Selective Histone Deacetylase Inhibitors and Antiproliferative Agents", J. Med. Chem., 2000, 43 (25), pp. 4919-4922, (Nov. 21, 2000), 4919-4922.
Ragan, John A., et al., "Safe Execution of a Large-Scale Ozonolysis:? Preparation of the Bisulfite Adduct of 2-Hydroxyindan-2-carboxaldehyde and Its Utility in a Reductive Amination", Org. Proc. Res. Dev., 2003, 7 (2), pp. 155-160, (Jan. 18, 2003), 155-160.

(Continued)

Primary Examiner — D Margaret M Seaman
(74) Attorney, Agent, or Firm — Schwegman Lundberg & Woessner, P.A.

(57) ABSTRACT

The present patent discloses a novel one pot two-step process for the synthesis of ivacaftor and related compounds of [Formula (I)], wherein $R^1$, $R^2$, $R^3$, $R^4$, $R^5$, $R^6$, $R^7$ and $Ar_1$ are as described above; its tautomers or pharmaceutically acceptable salts thereof starting from indole acetic acid amides.

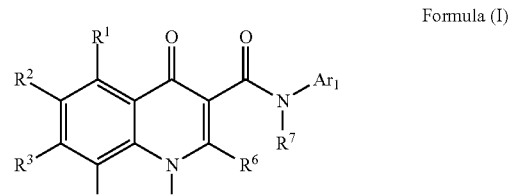

Formula (I)

12 Claims, No Drawings

(56) References Cited

OTHER PUBLICATIONS

Thompson, Mark, et al., "Structure-Activity Relationship Refinement and Further Assessment of Indole-3-glyoxylamides as a Lead Series against Prion Disease", ChemMedChem, vol. 6, No. 1, Jan. 3, 2011, pp. 115-130, (Jan. 3, 2011), 115-130.

Van Ornum, Scott G., et al., "Ozonolysis Applications in Drug Synthesis", Chem. Rev., 2006, 106 (7), pp. 2990-3001, (Jun. 20, 2006), 2990-3001.

Vasudevan, N., et al., "Breaking and Making of Rings: A Method for the Preparation of 4-Quinolone-3-carboxylic Acid Amides and the Expensive Drug Ivacaftor", European Journal of Organic Chemistry, vol. 2015, Issue 34, Dec. 2015, pp. 7433-7437, (Nov. 3, 2015), 7433-7437.

* cited by examiner

PROCESS FOR THE SYNTHESIS OF IVACAFTOR AND RELATED COMPOUNDS

PRIORITY CLAIM TO RELATED APPLICATIONS

This application is a U.S. national stage application filed under 35 U.S.C. § 371 from International Application Serial No. PCT/IN2016/050137, which was filed 12 May 2016, and published as WO2016/181414 on 17 Nov. 2016, and which claims priority to India Application No. 1324/DEL/2015, filed 12 May 2015, which applications and publication are incorporated by reference as if reproduced herein and made a part hereof in their entirety, and the benefit of priority of each of which is claimed herein.

FIELD OF THE INVENTION

The present invention relates to a novel process for the synthesis of ivacaftor and related compounds of Formula (I). More particularly, the present invention relates to a novel one pot two-step process for the synthesis of Ivacaftor and related compounds of Formula (I),

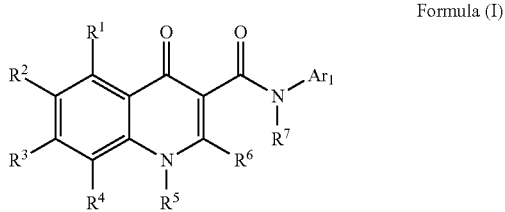

Formula (I)

wherein $R^1$, $R^2$, $R^3$, $R^4$, $R^5$, $R^6$, $R^7$ and $Ar^1$ are as described below;
its tautomers or pharmaceutically acceptable salts thereof starting from indole acetic acid amides.

BACKGROUND AND PRIOR ART

Ivacaftor, also known as N-(2,4-di-tert-butyl-5-hydroxyphenyl)-1,4-dihydro-4-oxoquinoline-3-carboxamide, having the following Formula (A):

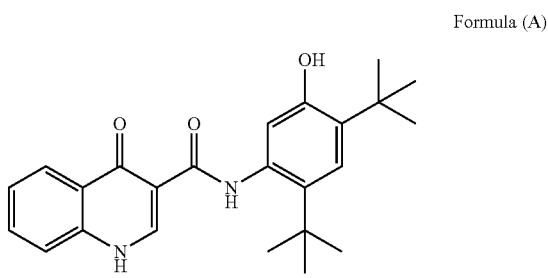 [SMILES: CC(C)(C)c1cc(C(C)(C)C)c(NC(=O)c2c[nH]c3ccccc3c2=O)cc1O]

Formula (A)

Ivacaftor was approved by FDA and marketed by vertex pharma for the treatment of cystic fibrosis under the brand name KALYDECO® in the form of 150 mg oral tablets. Kalydeco® is indicated for the treatment of cystic fibrosis in patients age 6 years and older who have a G55ID mutation in the CFTR (cystic fibrosis transmembrane conductance regulator) gene.

U.S. 20100267768 discloses a process for preparation of ivacaftor, which involves the coupling of 4-oxo-1,4-dihydro-3-quinoline carboxylic acid with hydroxyl protected phenol intermediate in the presence of propyl phosphonic anhydride ($T_3P$®) followed by deprotection of hydroxyl protection group and optional crystallization with isopropyl acetate. The publication also discloses the use of highly expensive coupling reagent, propyl phosphonic anhydride; which in turn results to an increase in the manufacturing cost. The process disclosed is schematically represented as follows:

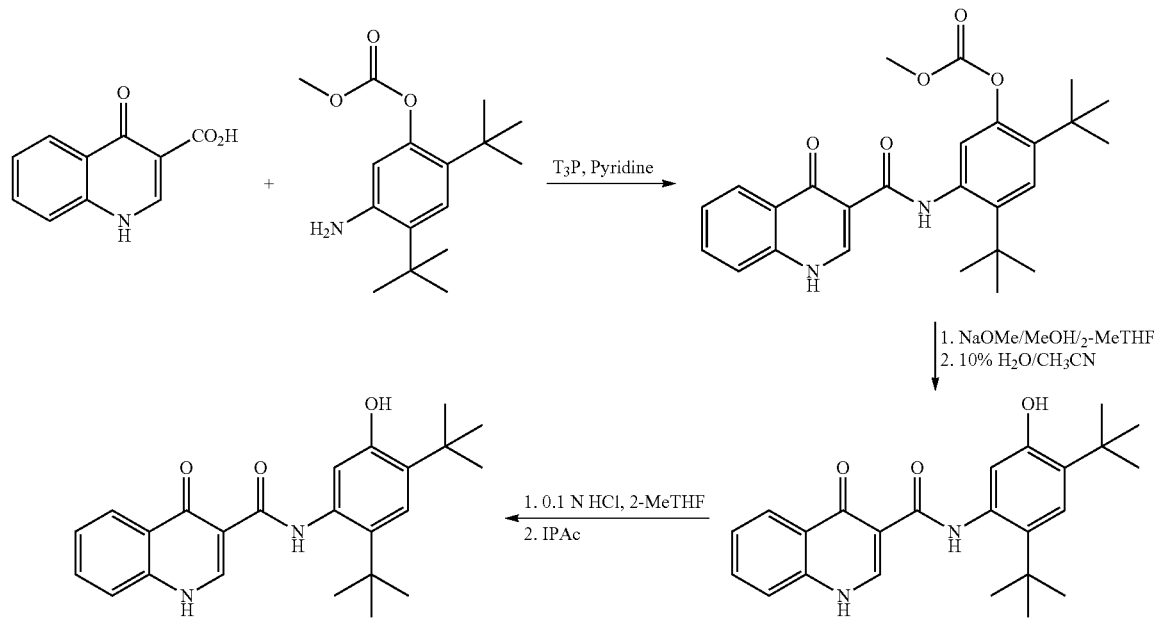

Article titled "Discovery of N-(2,4-Di-tert-butyl-5-hydroxyphenyl)-4-oxo-1,4-dihydroquinoline-3-carboxamide (VX-770, Ivacaftor), a Potent and Orally Bioavailable CFTR Potentiator" by Hadida, S et. al in *J. Med. Chem.*, 2014, 57

(23), pp 9776-9795 reports N-(2,4-di-tert-butyl-5-hydroxy-phenyl)-4-oxo-1,4-dihydroquinoline-3-carboxamide (VX-770, 48, ivacaftor), an investigational drug candidate approved by the FDA for the treatment of CF patients 6 years of age and older carrying the G551D mutation.

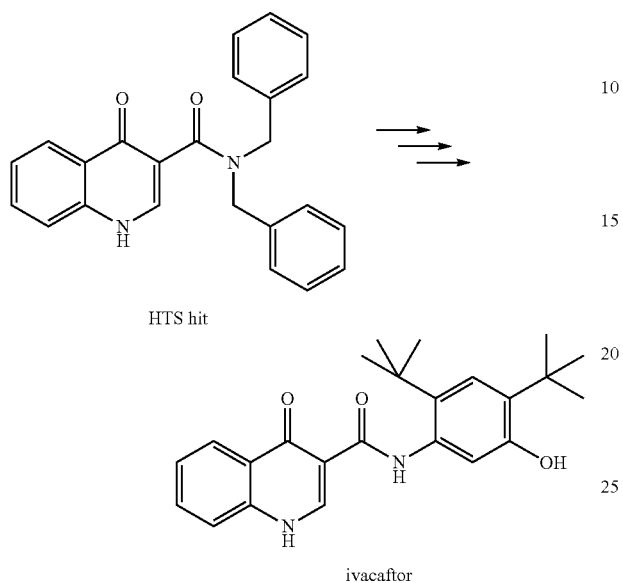

WO 2014125506 A2 discloses a process for the preparation of ivacaftor in high yield and purity by using novel protected quinolone carboxylic acid compounds as intermediates.

Article titled "Expeditious synthesis of ivacaftor" by Jingshan Shen et. al in *Heterocycles*, 2014, 89 (4), pp 1035-1040 reports an expeditious synthesis for ivacaftor featuring modified Leimgruber-Batcho procedure. The overall yield is 39% over six steps from commercially available 2-nitrobenzoyl chloride.

U.S. 2011/064811 discloses a process for preparation of ivacaftor, which involves condensation of 4-oxo-1,4-dihydro-3-quinolone carboxylic acid with 5-amino-2,4-di-(tert-butyl)phenol in the presence of HBTU followed by the formation of ethanol crystalate, which is then treated with diethyl ether to yield ivacaftor as a solid.

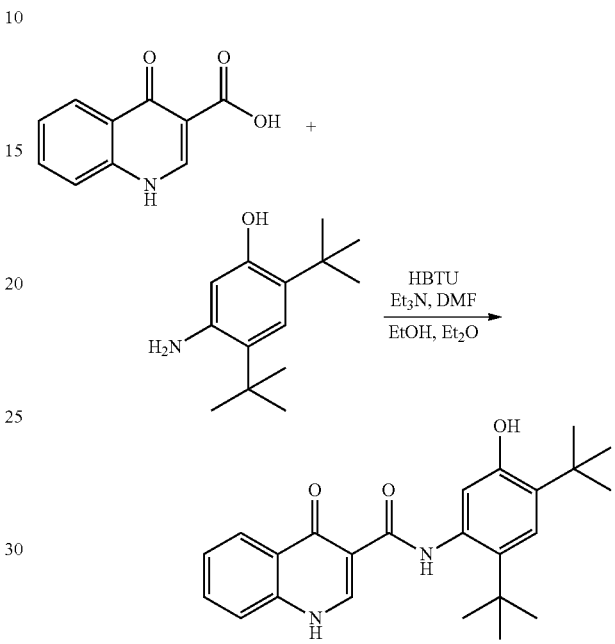

CN 103044263 A discloses a process for the preparation of ivacaftor as shown below:

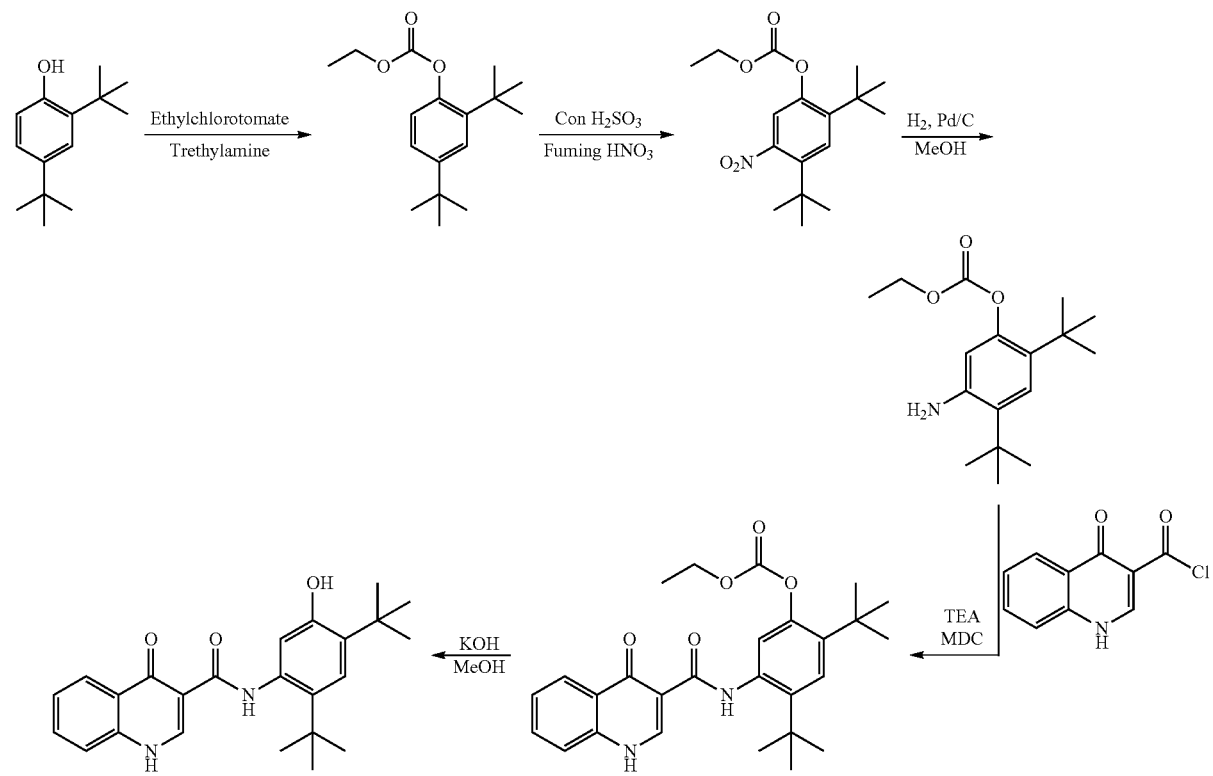

U.S. Pat. No. 7,495,103 discloses modulators of ATP-binding cassette transporters such as ivacaftor and a process for the preparation of modulators of ATP-binding cassette transporters such as quinolone compounds. The process includes condensation of 4-oxo-1,4-dihydro-3-quinolone carboxylic acid with aniline in presence of 2-(1H-7-azabenzotriazol-1-yl)-1,1,3,3-tetramethyluronium hexafluoro phosphate methanaminium (HATU) as shown:

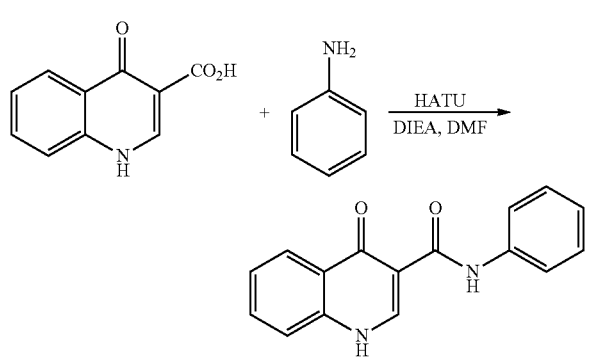

U.S. 2011/230519 discloses a process for preparation of 4-oxo-1,4-dihydro-3-quinoline carboxylic acid by reaction of aniline with diethylethoxymethylenemalonate at 100-110° C. followed by cyclization in phenyl ether at temperature 228-232° C. and then hydrolysis, as shown below:

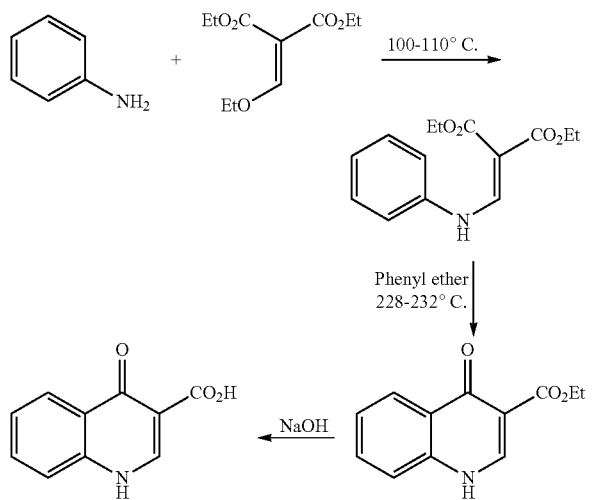

U.S. Pat. No. 7,402,674 B2 discloses 7-Phenylamino-4-quinolone-3-carboxylic acid derivatives, process for their preparation and their use as medicaments.

U.S. Pat. No. 4,981,854 discloses 1-aryl-4-quinolone-3 carboxylic acids, processes for their preparation and antibacterial agents and feed additives containing these compounds.

Article titled "Ozonolysis Applications in Drug Synthesis" by Van Ornum, S. G.; Champeau, R. M.; Pariza, R. in *Chem. Rev.*, 2006, 106 (7), pp 2990-3001 reports that ozonolysis for the synthesis of numerous interesting bioactive natural products and pharmaceutical agents.

Article titled "Safe Execution of a Large-Scale Ozonolysis: Preparation of the Bisulfite Adduct of 2-Hydroxyindan-2-carbox-aldehyde and Its Utility in a Reductive Amination" by Ragan, J. A. et. al. in *Org. Proc. Res. Dev.*, 2003, 7 (2), pp 155-160 reports various routes to bisulfite adduct, the most efficient of which involved vinyl Grignard addition to 2-indanone followed by ozonolysis and workup with aqueous $NaHSO_3$ to effect reduction and bisulfite formation in a single pot. The utility of bisulfite adduct is as an aldehyde surrogate in a reductive amination reaction.

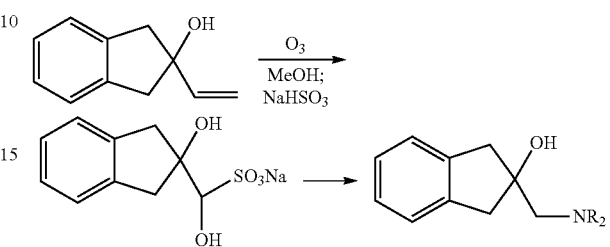

The reported methods for the synthesis of ivacaftor suffered from several drawbacks such as harsh conditions, high temperature reactions and use of large excess of polyphosphoric acid and corrosive phosphoryl chloride etc. Furthermore, synthesis of ivacaftor requires use of high performance liquid chromatography (HPLC) techniques for the separation of ivacaftor and their analogues.

Therefore, development of a simple and efficient synthetic route is in urgent need. Accordingly the present inventors developed environmentally benign, cost effective and short synthetic route for the synthesis of ivacaftor and their analogues.

OBJECTIVE OF THE INVENTION

The main objective of present invention is to provide a one pot process for the synthesis of compounds of Formula (I) starting from indole acetic acidamides at lower temperature.

Another objective of present invention is to provide a one pot process for the synthesis of ivacaftor starting from indole acetic acid amide at lower temperature.

SUMMARY OF THE INVENTION

Accordingly, the present invention provides a one pot process for the synthesis of compounds of Formula (I), its tautomers or pharmaceutically acceptable salts thereof starting from indole acetic acid amides at lower temperature.

In an aspect, the present invention provides a one pot process for the synthesis of ivacaftor starting from indole acetic acid amide at lower temperature.

DETAILED DESCRIPTION OF THE INVENTION

The invention will now be described in detail in connection with certain preferred and optional embodiments, so that various aspects thereof may be more fully understood and appreciated.

In view of above the present invention provides a one pot process for the preparation of compounds of Formula (I), its tautomers or pharmaceutically acceptable salts thereof.

In an embodiment, the present invention provides a one pot process for the preparation of compounds of Formula (I) and Formula (II),

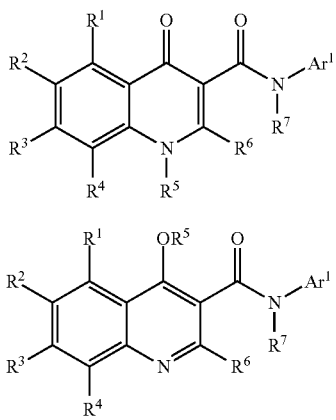

Formula (I)

Formula (II)

wherein, $Ar^1$ is a 5-6 membered aromatic/hetero aromatic ring, which could be further substituted by alkyl, aryl, hetero aryl and having 0-4 heteroatoms independently selected from nitrogen, oxygen, or sulfur, Wherein said ring is optionally fused to a 5-12 membered monocyclic or bicyclic, aromatic, partially unsaturated, or saturated ring, wherein each ring contains 0-4 heteroatoms independently selected from nitrogen, oxygen, or sulfur, wherein $Ar_1$ has m substituents, each independently selected from —$WR^W$; W is a bond or is an optionally substituted $C_1$-$C_6$ alkylidene chain wherein up to two methylene units of W are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR', —NR'NR'CO—, —NR'CO—, —S—, —SO, —$SO_2$—, —NR'—, —$SO_2$NR'—, NR'$SO_2$—, or —NR'$SO_2$NR'—; $R^W$ is independently R', halo, $NO_2$, CN, $CF_3$, or $OCF_3$; m is 0-5; each of $R^1$, $R^2$, $R^3$, $R^4$, and $R^5$ is hydrogen, —X—$R^X$; X is a bond or is an optionally substituted $C_1$-$C_6$ alkylidene chain wherein up to two methylene units of X are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR', —NR'NR'CO—, —NR'CO—, —S—, —SO, —$SO_2$—, —NR'—, —$SO_2$NR'—, NR'$SO_2$—, or —NR'$SO_2$NR'—; $R^X$ is independently R', halo, $NO_2$, CN, $CF_3$, or $OCF_3$; $R^6$ is hydrogen, $CF_3$, —OR', —SR', or an optionally substituted $C_{1-6}$ aliphatic group; $R^{7'}$ $R^8$ is hydrogen or a $C_{1-6}$ aliphatic group optionally substituted with —X—$R^X$; R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; its tautomers or pharmaceutically acceptable salts thereof.

In another embodiment, the present invention provides a one pot process for the synthesis of compounds of Formula (I), its tautomers or pharmaceutically acceptable salts thereof comprising the steps of:

a) coupling indole acetic acid with corresponding amines using suitable coupling agent to obtain indole amides;
b) oxidizing indole amides of step (a) using suitable oxidizing agent followed by treatment with base to obtain desired quinolone carboxamides.

In a preferred embodiment, the corresponding amines in step (a) are compounds of Formula $Ar_1$—NH—$R^7$, Wherein $Ar^1$ is a 5-6 membered aromatic/hetero aromatic ring, which could be further substituted by alkyl, aryl, hetero aryl and having 0-4 heteroatoms independently selected from nitrogen, oxygen, or sulfur, wherein said ring is optionally fused to a 5-12 membered monocyclic or bicyclic, aromatic, partially unsaturated, or saturated ring, Wherein each ring contains 0-4 heteroatoms independently selected from nitrogen, oxygen, or sulfur, wherein $Ar_1$ has m substituents, each independently selected from —$WR^W$; W is a bond or is an optionally substituted $C_1$-$C_6$ alkylidene chain wherein up to two methylene units of W are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR'NR', —NR'NR'CO—, —NR'CO—, —S—, —SO, —$SO_2$—, —NR'—, —$SO_2$NR'—, NR'$SO_2$—, or —NR'$SO_2$NR'—; $R^W$ is independently R', halo, $NO_2$, CN, $CF_3$, or $OCF_3$; m is 0-5; $R^7$, $R^8$ is hydrogen or a $C_{1-6}$ aliphatic group optionally substituted with —X—$R^X$; and $R^X$ is independently R', halo, $NO_2$, CN, $CF_3$, or $OCF_3$.

In another preferred embodiment, the suitable coupling agent in step (a) is selected from HATU (1-[bis(dimethylamino)methylene]-1H-1,2,3-triazolo[4,5-b]pyridinium 3-oxid hexafluoro phosphate) or HBTU (O-benzotriazole-N,N,N',N'-tetramethyl-uronium-hexafluoro-phosphate), hydroxybenzotriazole or (EDC) 1-ethyl-3-(3-dimethylaminopropyl)carbodiimide or DCC (N,N'-dicyclohexylcarbodiimide), or DIC (N,N'-diisopropylcarbodiimide) or CDI (1,1'-carbonyldiimidazole) or TBTU (O-(benzotriazol-1-yl)-N,N,N',N'-tetramethyluroniumtetrafluoroborate) or FDPP (pentafluorophenyldiphenylphosphinate); preferably carbodiimides.

In yet another preferred embodiment, the suitable oxidizing agent in step (b) is selected from sodium periodate, peroxides, potassium permanganate, $CrO_3$, ozone and the like; preferably ozone.

In still another preferred embodiment, the base in step (b) is organic base and is selected from pyridine, 2,6-lutidine, DMAP (4-dimethylaminopyridine), $Et_3N$ (triethylamine), DIPEA (N,N-diisopropyl ethyl amine), N,N-dimethylaniline, DBN (1,5-diazabicyclo(4.3.0)non-5-ene), DABCO (1,4-diazabicyclo[2.2.2]octane) and DBU (1,8-diazabicycloundec-7-ene) or mixture thereof; preferably pyridine or triethylamine.

In a more preferred embodiment, the present invention provides a one pot process for the synthesis of compounds of Formula (I), its tautomers or pharmaceutically acceptable salts thereof comprising the steps of:

a) adding EDC.HCl and DIPEA to a solution of indole acetic acid, aniline and HOBt in acetonitrile followed by stirring the reaction mixture for 16 h at room temperature to obtain indole amides;
b) passing the a stream of $O_3$ to a solution of compound of step (a) in DCM:MeOH and adding pyridine and triethylamine followed by stirring the reaction mixture for overnight at room temperature to obtain desired compounds.

In an aspect, the quinolone carboxamide compound is selected from 4-oxo-N-phenyl-1,4-dihydroquinoline-3-carboxamide (23), 2,4-di-tert-butyl-5-(4-oxo-1,4-dihydroquinoline-3-carboxamido)phenyl methyl carbonate (24), (S)-4-oxo-N-(1-phenylethyl)-1,4-dihydroquinoline-3-carboxamide (25), N-(4-fluorophenyl)-4-oxo-1,4-dihydroquinoline-3-carboxamide (27), N-(4-chlorophenyl)-4-oxo-1,4-dihydroquinoline-3-carboxamide (28), 4-oxo-N-(p-tolyl)-1,4-dihydroquinoline-3-carboxamide (29), N-(4-ethylphenyl)-4-oxo-1,4-dihydroquinoline-3-carboxamide (30), 4-Oxo-N-(4-propylphenyl)-1,4-dihydroquinoline-3-carboxamide (31), N-(4-isopropylphenyl)-4-oxo-1,4-dihydroquinoline-3-carboxamide (32), 4-oxo-N-(4-(trifluoromethoxy)phenyl)-1,4-dihydroquinoline-3-carboxamide (33), N-(2-chloro-5-methoxyphenyl)-4-oxo-1,4-dihydroquinoline-3-carboxamide (34), N-(2-ethylphenyl)-4-oxo-1,4-dihydroquinoline-3-carboxamide (35), N-(2-bromophenyl)-4-oxo-1,4-dihydroquinoline-3-carboxamide (36), N-benzyl-4-oxo-1,4-dihydroquinoline-3-carboxamide (37), N-(4-methoxybenzyl)-4-oxo-1,4-dihydroquinoline-3-carboxamide (38), N,N-dibenzyl-4-oxo-1,4-dihydroquinoline-3-carboxamide (39), 4-oxo-N-propyl-1,4-dihydroquinoline-3-carboxamide (40), N-hexyl-4-oxo-1,4-dihydroquinoline-3-carboxamide (41), Methyl (4-oxo-1,4-dihydroquinoline-3-carbonyl)-L-alaninate (42), 7-chloro-4-oxo-N-phenyl-1,4-dihydroquinoline-3-carboxamide (43), 6-chloro-4-oxo-N-phenyl-1,4-dihydroquinoline-3-carboxamide (44), 1-benzyl-4-oxo-N-phenyl-1,4-dihydroquinoline-3-carboxamide (45).

In another aspect, the indole amides is selected from 2-(1H-indol-3-yl)-N-phenylacetamide (1), 5-(2-(1H-indol-3-yl)acetamido)-2,4-di-tert-butylphenyl methyl carbonate (2), (S)-2-(1H-indol-3-yl)-N-(1-phenylethyl)acetamide (3), N-(4-Fluorophenyl)-2-(1H-indol-3-yl)acetamide (4), N-(4-Chlorophenyl)-2-(1H-indol-3-yl)acetamide (5), 2-(1H-Indol-3-yl)-N-(p-tolyl)acetamide (6), N-(4-Ethylphenyl)-2-(1H-indol-3-yl)acetamide (7), 2-(1H-Indol-3-yl)-N-(4-propylphenyl)acetamide (8), 2-(1H-Indol-3-yl)-N-(4-isopropylphenyl)acetamide (9), 2-(1H-indol-3-yl)-N-(4-(trifluoromethoxy)phenyl)acetamide (10), N-(2-chloro-5-methoxyphenyl)-2-(1H-indol-3-yl)acetamide (11), N-(2-ethylphenyl)-2-(1H-indol-3-yl)acetamide (12), N-(2-bromophenyl)-2-(1H-indol-3-yl)acetamide (13), N-benzyl-2-(1H-indol-3-yl)acetamide (14), 2-(1H-indol-3-yl)-N-(4-methoxybenzyl)acetamide (15), N,N-dibenzyl-2-(1H-indol-3-yl)acetamide (16), 2-(1H-indol-3-yl)-N-propylacetamide (17), N-hexyl-2-(1H-indol-3-yl)acetamide (18), Methyl (2-(1H-indol-3-yl)acetyl)-L-alaninate (19), 2-(6-chloro-1H-indol-3-yl)-N-phenylacetamide (20), 2-(5-chloro-1H-indol-3-yl)-N-phenylacetamide (21), 2-(1-benzyl-1H-indol-3-yl)-N-phenylacetamide (22).

The process for the synthesis of compounds of Formula (I) is as depicted in scheme 1:

Scheme 1

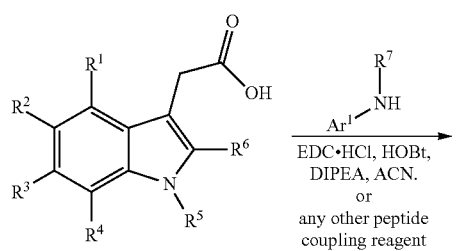

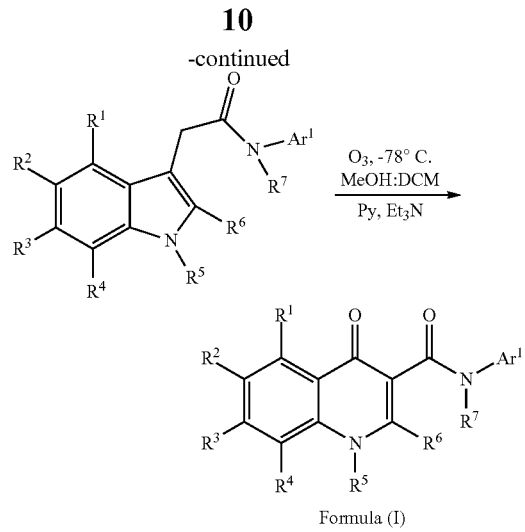

Formula (I)

In yet another embodiment, the present invention provides a one pot process for the synthesis of ivacaftor starting from indole acetic acid comprising the steps of:
  a) coupling indole acetic acid with corresponding amine using suitable coupling agent;
  b) oxidizing indole amides of step (a) using suitable oxidizing agent followed by treatment with base to obtain quinolone carboxamides;
  c) deprotection of phenol in the quinolone carboxamides of step (b) under basic condition to afford ivacaftor.

In a preferred embodiment, the corresponding amine in step (a) is aniline or derivative thereof.

In another preferred embodiment, the suitable coupling agent in step (a) is selected from HATU (1-[bis(dimethylamino)methylene]-1H-1,2,3-triazolo[4,5-b]pyridinium 3-oxid hexafluoro phosphate) or HBTU (O-benzotriazole-N,N,N',N'-tetramethyl-uronium-hexafluoro-phosphate), hydroxybenzotriazole or (EDC) 1-ethyl-3-(3-dimethylaminopropyl)carbodiimide or DCC (N,N'-dicyclohexylcarbodiimide), or DIC (N,N'-diisopropylcarbodiimide) or CDI (1,1'-carbonyldiimidazole) or TBTU (O-(benzotriazol-1-yl)-N,N,N',N'-tetramethyluroniumtetrafluoroborate) or FDPP (pentafluorophenyldiphenylphosphinate); preferably carbodiimides.

In yet another preferred embodiment, the suitable oxidizing agent in step (b) is selected from sodium periodate, peroxides, potassium permanganate, chromium trioxide, ozone and the like; preferably ozone.

In still another preferred embodiment, the base in step (b) is organic base and is selected from pyridine, 2,6-lutidine, DMAP (4-dimethylaminopyridine), Et$_3$N (triethylamine), DIPEA (N,N-diisopropyl ethyl amine), N,N-dimethylaniline, DBN (1,5-diazabicyclo(4.3.0)non-5-ene), DABCO (1,4-diazabicyclo[2.2.2]octane) and DBU (1,8-diazabicycloundec-7-ene) or mixture thereof; preferably pyridine or triethylamine.

In a more preferred embodiment, the present invention provides process for the synthesis of ivacaftor comprising the step of:
  a) adding EDC.HCl and DIPEA to a solution of indole acetic acid, aniline and HOBt in acetonitrile followed by stirring the reaction mixture for 16 h at room temperature to obtain 5-(2-(1H-indol-3-yl)acetamido)-2,4-di-tert-butylphenyl methyl carbonate (2);
  b) passing the a stream of O$_3$ to a solution of compound of step (a) in DCM:MeOH and adding pyridine and Et$_3$N followed by stirring the reaction mixture for overnight at room temperature to obtain 2,4-di-tert-butyl-5-(4-oxo-1,4-dihydroquinoline-3-carboxamido)phenyl methyl carbonate (5);

c) adding NaOH dissolved in H$_2$O to a solution of compound of step (b) in methanol followed by stirring the reaction mixture for 5 h at room temperature to obtain ivacaftor.

The process for the synthesis of ivacaftor is as depicted in scheme 2:

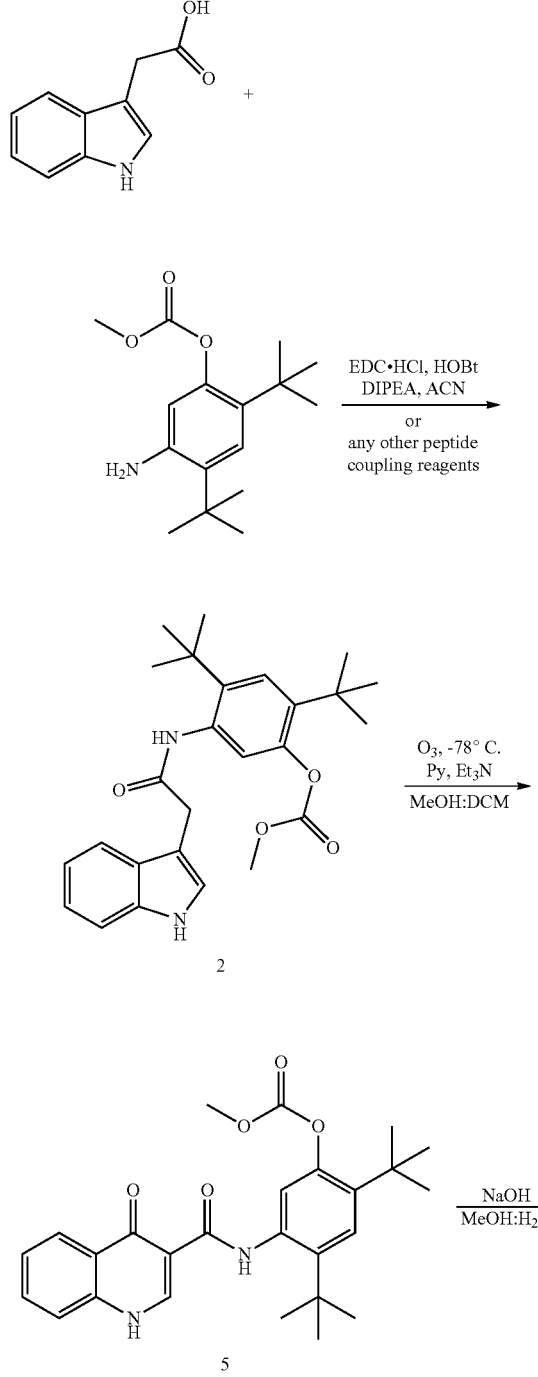

Scheme 2

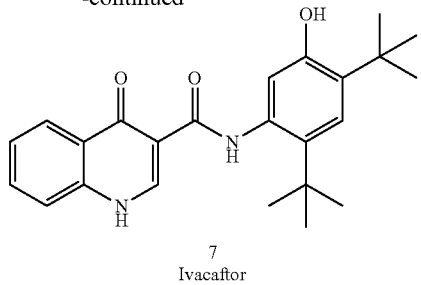

7
Ivacaftor

The following examples, which include preferred embodiments, will serve to illustrate the practice of this invention, it being understood that the particulars shown are by way of example and for purpose of illustrative discussion of preferred embodiments of the invention.

EXAMPLES

Example 1

Procedure A:

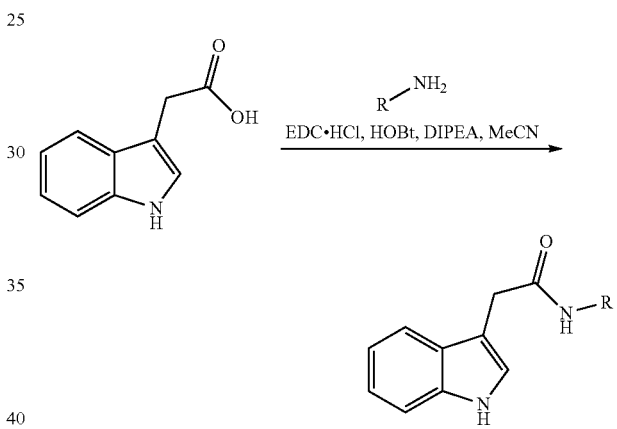

To a solution of indole acetic acid (500 mg, 2.85 mmol), aniline (2.85 mmol), HOBt (3.4 mmol) in acetonitrile (10 mL), EDC.HCl (3.4 mmol) followed by DIPEA (11.4 mmol) was added, and mixture was stirred for 16 h at ambient temperature. The reaction mixture was evaporated to dryness, diluted with EtOAc (25 mL), washed with saturated aqueous NaHCO$_3$ solution (5 mL), H$_2$O (5 mL), brine (5 mL), and dried over Na$_2$SO$_4$. The crude material obtained after removal of solvent was purified by column chromatography (silica gel 230-400 mesh, ethyl acetate-pet ether) to afford corresponding amide as a colorless solid.

Example 2

2-(1H-indol-3-yl)-N-phenylacetamide (1)

Yield: 570 mg; 80%; $^1$H NMR (200 MHz, DMSO-d$_6$) δ=10.95 (brs, 1H), 10.14 (s, 1H), 7.64 (d, J=7.8 Hz, 3H), 7.47-7.24 (m, 4H), 7.21-6.92 (m, 3H), 3.76 (s, 2H); MS: 273 (M+Na)$^+$.

Example 3

5-(2-(1H-indol-3-yl)acetamido)-2,4-di-tert-butylphenyl Methyl Carbonate (2)

Yield: 800 mg; 64%; $^1$H NMR (200 MHz, DMSO-d$_6$) δ=11.51 (brs, 1H), 9.41 (s, 1H), 8.12 (d, J=7.6 Hz, 1H), 7.96-7.78 (m, 3H), 7.71-7.42 (m, 3H), 4.34 (s, 3H), 4.30 (s, 2H), 1.79 (s, 9H), 1.64 (s, 9H); MS: 459 (M+Na)$^+$.

Example 4

(S)-2-(1H-indol-3-yl)-N-(1-phenylethyl)acetamide (3)

Yield: 620 mg; 78%; $^1$H NMR (400 MHz, DMSO-d$_6$) δ=10.88 (brs, 1H), 8.48 (d, J=8.1 Hz, 1H), 7.59 (d, J=7.8 Hz, 1H), 7.39-7.26 (m, 5H), 7.25-7.16 (m, 2H), 7.08 (t, J=7.3 Hz, 1H), 7.02-6.95 (m, 1H), 4.96 (t, J=7.3 Hz, 1H), 3.59 (s, 2H), 1.38 (d, J=7.1 Hz, 3H).

Example 5

N-(4-Fluorophenyl)-2-(1H-indol-3-yl)acetamide (4)

$^1$H NMR (400 MHz, DMSO-d$_6$): δ 10.93 (brs, 1H), 10.17 (s, 1H), 7.68-7.61 (m, 3H), 7.36 (d, J=8.1 Hz, 1H), 7.27 (d, J=2.0 Hz, 1H), 7.15-7.13 (m, 3H), 7.11-6.99 (m, 1H), 3.73 (s, 2H); $^{13}$C NMR (100 MHz, DMSO-d$_6$): δ 170.1, 159.5, 157.1, 136.6, 136.3, 127.7, 124.4, 121.5, 121.3, 121.2, 119.1, 118.9, 115.8, 115.6, 111.8, 108.9, 34.2; MS: 269 (M+H)$^+$

Example 6

N-(4-Chlorophenyl)-2-(1H-indol-3-yl)acetamide (5)

$^1$H NMR (200 MHz, DMSO-d$_6$): δ10.93 (brs, 1H), 10.24 (s, 1H), 7.67-7.59 (m, 3H), 7.36-7.27 (m, 4H), 7.12-6.98 (m, 2H), 3.74 (s, 2H); $^{13}$CNMR (100 MHz, DMSO-d$_6$): δ170.4, 138.9, 136.7, 129.1, 127.8, 127.1, 124.5, 121.6, 121.2, 119.2, 119.0, 115.7, 111.9, 108.9, 34.3; MS: 285 (M+H)$^+$.

Example 7

2-(1H-Indol-3-yl)-N-(p-tolyl)acetamide (6)

$^1$H NMR (400 MHz, DMSO-d$_6$): δ10.91 (brs, 1H), 10.01 (s, 1H), 7.62 (d, J=7.8 Hz, 1H), 7.50 (d, J=8.6 Hz, 2H), 7.37 (d, J=8.1 Hz, 1H), 7.29-7.26 (m, 1H), 7.10-7.07 (m, 3H), 7.01-6.99 (m, 1H), 3.71 (s, 2H), 2.23 (s, 3H); $^{13}$C NMR (100 MHz, DMSO-d$_6$): δ170.0, 137.4, 136.6, 132.4, 129.5, 127.7, 124.3, 121.4, 119.6, 119.2, 118.8, 111.8, 109.1, 34.2, 20.9; MS: 265 (M+H)$^+$.

Example 8

N-(4-Ethylphenyl)-2-(1H-indol-3-yl)acetamide (7)

$^1$H NMR (400 MHz, DMSO-d$_6$): δ10.91 (brs, 1H), 10.01 (s, 1H), 7.61 (s, 1H), 7.52 (d, J=8.3 Hz, 2H), 7.36 (d, J=8.1 Hz, 1H), 7.26 (s, 1H), 7.15-7.04 (m, 3H), 6.99 (s, 1H), 2.55 (t, J=7.5 Hz, 2H), 1.15 (t, J=7.5 Hz, 3H); $^{13}$C NMR (100 MHz, DMSO-d$_6$): δ169.9, 138.9, 137.6, 136.6, 128.3, 127.7, 124.3, 121.4, 119.6, 119.2, 118.8, 111.8, 109.1, 40.6, 40.4, 40.2, 40.0, 39.8, 39.6, 39.4, 34.2, 28.0, 16.2; MS: 279 (M+H)$^+$.

Example 9

2-(1H-Indol-3-yl)-N-(4-propylphenyl)acetamide (8)

$^1$H NMR (400 MHz, DMSO-d$_6$): δ8.48 (brs, 1H), 7.64 (d, J=8.1 Hz, 1H), 7.50-7.42 (m, 2H), 7.33-7.15 (m, 6H), 7.07 (d, J=8.3 Hz, 2H), 3.92 (s, 2H), 2.52 (t, J=7.6 Hz, 2H), 1.65-1.53 (m, 2H), 0.91 (t, J=7.3 Hz, 3H); $^{13}$C NMR (100 MHz, DMSO-d$_6$): δ169.7, 138.9, 136.5, 135.2, 128.8, 126.9, 124.0, 122.8, 120.4, 120.1, 118.7, 111.6, 108.7, 37.4, 34.5, 24.6, 13.7; MS: 315 (M+Na)$^+$.

Example 10

2-(1H-Indol-3-yl)-N-(4-isopropylphenyl)acetamide (9)

yield 79%; $^1$H NMR (400 MHz, DMSO-d$_6$): δ 10.91 (brs, 1H), 10.01 (s, 1H), 7.62 (d, J=7.8 Hz, 1H), 7.55-7.49 (m, J=8.6 Hz, 2H), 7.37 (d, J=8.1 Hz, 1H), 7.26 (d, J=2.0 Hz, 1H), 7.18-7.11 (m, J=8.6 Hz, 2H), 7.11-7.05 (m, 1H), 7.02-6.95 (m, 1H), 2.95-2.71 (m, 1H), 1.17 (d, J=6.8 Hz, 6H); $^{13}$C NMR (100 MHz, DMSO-d$_6$): δ 169.9, 143.5, 137.6, 136.6, 127.7, 126.8, 124.3, 121.4, 119.7, 119.2, 118.8, 111.8, 109.2, 24.4; MS: 315 (M+Na)$^+$.

Example 11

2-(1H-indol-3-yl)-N-(4-(trifluoromethoxy)phenyl) acetamide (10)

Yield 85%; $^1$H NMR (400 MHz, CDCl$_3$): δ 8.35 (brs., 1H), 7.44-7.38 (m, 2H), 7.27-7.21 (m, 3H), 7.12-7.05 (m, 1H), 7.03-6.95 (m, 2H), 6.93 (d, J=8.6 Hz, 2H), 3.75 (s, 2H); $^{13}$C NMR (100 MHz, CDCl$_3$): δ 170.0, 145.3, 136.5, 136.2, 126.8, 124.1, 123.0, 121.6, 121.2, 120.5, 118.5, 111.7, 108.2, 34.4; MS: 335 (M+Na)$^+$.

Example 12

N-(2-chloro-5-methoxyphenyl)-2-(1H-indol-3-yl) acetamide (11)

Yield 75%; $^1$H NMR (200 MHz, DMSO-d$_6$): δ 10.98 (brs, 1H), 9.27 (s, 1H), 7.59 (d, J=7.8 Hz, 1H), 7.53 (d, J=2.9 Hz, 1H), 7.39-7.32 (m, 3H), 7.09-6.99 (m, 2H), 6.74 (dd, J=3.0, 8.8 Hz, 1H), 3.85 (s, 2H), 3.71 (s, 3H); $^{13}$C NMR (400 MHz, DMSO-d$_6$): δ 170.4, 160.1, 141.1, 136.7, 130.0, 127.8, 124.4, 121.6, 119.2, 119.0, 111.9, 109.1, 105.4, 55.4, 34.4; MS: 315 (M+Na)$^+$.

Example 13

N-(2-ethylphenyl)-2-(1H-indol-3-yl)acetamide (12)

Yield 78%; $^1$H NMR (400 MHz, CDCl$_3$): δ 8.68 (brs, 1H), 7.95 (d, J=8.1 Hz, 1H), 7.67 (d, J=7.8 Hz, 1H), 7.48-7.44 (m, 2H), 7.29-7.23 (m, 1H), 7.22-7.20 (m, 3H), 7.05 (d, J=4.4 Hz, 2H), 2.00 (q, J=7.4 Hz, 2H), 0.67 (t, J=7.6 Hz, 3H); $^{13}$C NMR (100 MHz, CDCl$_3$): δ 169.9, 136.6, 135.0, 134.3, 128.7, 126.7, 125.1, 124.1, 123.0, 122.5, 120.4, 118.7, 111.6, 108.6, 34.4, 24.2, 13.6.

Example 14

N-(2-bromophenyl)-2-(1H-indol-3-yl)acetamide (13)

Yield 76%; $^1$H NMR (200 MHz, DMSO-d$_6$): δ 11.00 (brs, 1H), 9.30 (s, 1H), 7.81-7.77 (m, 1H), 7.63-7.56 (m, 2H), 7.41-7.35 (m, 3H), 7.11-7.05 (m, 3H), 3.85 (s, 2H); $^{13}$C NMR (100 MHz, DMSO-d$_6$): δ 169.9, 136.2, 132.5, 128.0, 127.2, 126.4, 125.5, 124.4, 121.2, 118.7, 118.5, 116.4, 111.4, 108.0, 33.2.

Example 15

N-benzyl-2-(1H-indol-3-yl)acetamide (14)

Yield 85%; $^1$H NMR (400 MHz, DMSO-d$_6$): δ 10.89 (brs., 1H), 8.40 (t, J=5.7 Hz, 1H), 7.57 (d, J=7.8 Hz, 1H), 7.36 (d, J=8.1 Hz, 1H), 7.32-7.18 (m, 6H), 7.08 (t, J=7.5 Hz, 1H), 7.03-6.90 (m, 1H), 4.28 (d, J=5.9 Hz, 2H), 3.60 (s, 2H); $^{13}$C NMR (100 MHz, DMSO-d$_6$): δ 171.2, 140.1, 136.6, 128.7, 127.7, 127.2, 124.3, 121.4, 119.2, 118.7, 111.8, 109.3, 42.7, 33.2.

Example 16

2-(1H-indol-3-yl)-N-(4-methoxybenzyl)acetamide (15)

Yield 85%; $^1$H NMR (400 MHz, DMSO-d$_6$): δ 10.87 (brs, 1H), 8.32 (t, J=5.6 Hz, 1H), 7.55 (d, J=7.8 Hz, 1H), 7.35 (d, J=8.1 Hz, 1H), 7.22-7.13 (m, 3H), 7.11-7.05 (m, 1H), 7.00-6.94 (m, 1H), 6.84 (d, J=8.6 Hz, 2H), 4.20 (d, J=6.1 Hz, 2H), 3.72 (s, 3H), 3.56 (s, 2H); $^{13}$C NMR (100 MHz, DMSO-d$_6$): δ 171.1, 158.6, 136.6, 132.0, 129.0, 127.7, 124.2, 121.4, 119.2, 118.7, 114.1, 111.8, 109.4, 55.5, 42.1, 33.2.

Example 17

N,N-dibenzyl-2-(1H-indol-3-yl)acetamide (16)

Yield 70%; $^1$H NMR (400 MHz, DMSO-d$_6$): δ 10.91 (brs, 1H), 7.50 (d, J=7.8 Hz, 1H), 7.37-7.34 (m, 3H), 7.30 (d, J=6.6 Hz, 1H), 7.25-7.19 (m, 3H), 7.17 (t, J=6.6 Hz, 5H), 7.16 (d, J=7.8 Hz, 1H), 7.00-6.97 (m, 1H), 4.59 (s, 2H), 4.50 (s, 2H), 3.86 (s, 2H); $^{13}$C NMR (100 MHz, DMSO-d$_6$): δ 171.7, 138.2, 136.6, 129.2, 128.8, 128.1, 127.8, 127.7, 127.5, 127.1, 124.2, 121.5, 119.2, 118.8, 111.8, 108.5, 50.7, 48.4, 31.2.

Example 18

2-(1H-indol-3-yl)-N-propylacetamide (17)

Yield 75%; $^1$H NMR (200 MHz, DMSO-d$_6$): δ 10.86 (brs, 1H), 7.88-7.80 (m, 1H), 7.56 (d, J=7.6 Hz, 1H), 7.31 (d, J=7.8 Hz, 1H), 7.17 (d, J=2.3 Hz, 1H), 7.06-6.92 (m, 2H), 3.48 (s, 2H), 3.00 (q, J=6.8 Hz, 2H), 1.39 (sxt, J=7.2 Hz, 2H), 0.88-0.75 (t, J=7.2 Hz, 3H); $^{13}$C NMR (100 MHz, DMSO-d$_6$): δ 171.0, 136.6, 127.8, 124.2, 121.4, 119.2, 118.7, 111.8, 109.6, 39.4, 33.3, 22.9, 11.9.

Example 19

N-hexyl-2-(1H-indol-3-yl)acetamide (18)

Yield 87%; $^1$H NMR (400 MHz, DMSO-d$_6$): δ 10.84 (brs, 1H), 7.83 (brs, 1H), 7.54 (d, J=7.8 Hz, 1H), 7.33 (d, J=8.1 Hz, 1H), 7.21-7.13 (m, 1H), 7.06 (t, J=7.6 Hz, 1H), 6.96 (t, J=7.5 Hz, 1H), 3.47 (s, 2H), 3.03 (q, J=6.8 Hz, 2H), 1.37 (t, J=6.5 Hz, 2H), 1.30-1.15 (m, 6H), 0.84 (t, J=6.7 Hz, 3H); $^{13}$C NMR (100 MHz, DMSO-d$_6$): δ 170.9, 136.6, 127.7, 124.2, 121.3, 119.1, 118.7, 111.7, 109.5, 39.06, 33.2, 31.5, 29.6, 26.5, 22.5, 14.4.

Example 20

Methyl (2-(1H-indol-3-yl)acetyl)-L-alaninate (19)

Yield 79%; $^1$H NMR (400 MHz, CDCl$_3$): δ 8.53 (brs, 1H), 7.60 (d, J=7.8 Hz, 1H), 7.41 (d, J=8.1 Hz, 1H), 7.25-7.23 (m, 1H), 7.19-7.14 (m, 2H), 6.27 (d, J=7.3 Hz, 1H), 4.63 (t, J=7.3 Hz, 1H), 3.78 (s, 2H), 3.68 (s, 3H), 1.31 (d, J=7.3 Hz, 3H); $^{13}$C NMR (100 MHz, CDCl$_3$): δ 173.4, 171.2, 136.4, 127.0, 123.8, 122.5, 119.9, 118.7, 111.5, 108.5, 52.4, 48.0, 33.3, 18.2.

Example 21

2-(6-chloro-1H-indol-3-yl)-N-phenylacetamide (20)

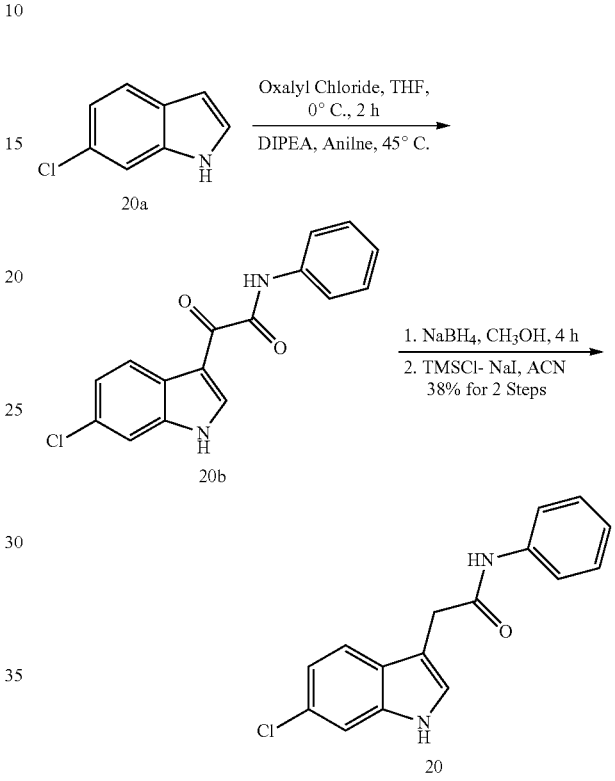

To a solution of 6-Chloro indole 20a (300 mg, 1.98 mmol) in anhydrous THF, Oxalyl chloride (186 μL, 276 mg, 2.18 mmol) was added and the mixture stirred at room temperature. After 2 h, N,N-Diisopropylethylamine (758 μL, 562 mg, 4.35 mmol) was introduced to the mixture, followed by the aniline (221.0 mg, 2.37 mmol). The temperature was raised to 45° C., and heating continued for 18 h. The solvent was evaporated, and then mixture was diluted with EtOAC (15 mL), washed with brine and dried over anhydrous Na$_2$SO$_4$. The crude material obtained after removal of solvent was purified by column chromatography (10-20% EtOAc:Petroleum ether) to afford 20b (295 mg, 51% yield) as a yellow coloured solid. IR υ$_{max}$ (film): 3346, 3307, 2853, 1724, 1678 cm$^{-1}$; $^1$H NMR (400 MHz, DMSO-d$_6$): δ 12.40 (br. s., 1H), 10.68 (s, 1H), 8.79 (d, J=3.2 Hz, 1H), 8.25 (d, J=8.6 Hz, 1H), 7.85 (d, J=7.8 Hz, 2H), 7.62 (d, J=1.7 Hz, 1H), 7.41-7.30 (m, 3H), 7.19-7.13 (m, 1H); $^{13}$C NMR (100 MHz, DMSO-d$_6$): δ 182.5, 162.5, 140.0, 138.4, 137.4, 129.2, 128.5, 125.4, 124.8, 123.4, 122.9, 120.8, 113.0, 112.3; HRMS (ESI) Calculated for C$_{16}$H$_{11}$N$_2$OCl[M+H]$^+$: 299.0582, found 299.0580;

A solution of 20b (300 mg, 0.99 mmol) dissolved in MeOH (40 mL) was added to NaBH$_4$ (45 mg, 1.23 mmol). The reaction was stirred for 4 h and then added to saturated solution of Na$_2$SO$_4$. The reaction mixture was further stirred for 1 h and then filtered through Celite. The filtrate obtained was concentrated in vacuo, and then mixture was diluted with EtOAc (15 mL), washed with brine and dried over anhydrous $Na_2SO_4$. The crude material obtained after removal of solvent was forwarded for next step without further purification. In an $N_2$ atmosphere, TMSCl (1.272 mL, 9.9 mmol) in $CH_3CN$ (40 mL) was added to sodium iodide (1.488 mg, 9.9 mmol) and stirred for 2 h. The reaction mixture was cooled to 0° C. and a solution of above crude alcohol (0.99 mmol) in $CH_3CN$ (10 mL) was then added dropwise over 30 min, followed by stirring for 3 h. The reaction mixture was poured into NaOH (7 g in 40 mL of water) and then extracted with ethyl acetate (15×2). The organic layer was washed with aq.$Na_2S_2O_3$, dried over $Na_2SO_4$ and concentrated in vacuo. The residue was chromatographed on silica gel (EtOAc:Pet ether) to afford 20 as a off white solid (two steps 38%); IR $\upsilon_{max}$ (film): 3273, 3084, 2953, 2857, 1629, 1562 cm$^{-1}$; $^1$H NMR (400 MHz, DMSO-$d_6$): δ 11.06 (br. s., 1H), 10.13 (br. s., 1H), 7.62-7.57 (m, 3H), 7.40 (s, 1H), 7.30-7.25 (m, 3H), 7.04-6.99 (m, 2H), 3.71 (s, 2H); $^{13}$C NMR (100 MHz, DMSO-$d_6$): δ 170.1, 139.7, 136.9, 129.2, 126.5, 126.3, 125.5, 123.7, 120.6, 119.6, 119.3, 111.5, 109.4, 34.0; HRMS (ESI): Calculated for $C_{16}H_{14}N_2OCl[M+H]^+$: 285.0789, found 285.0786.

Example 22

2-(5-chloro-1H-indol-3-yl)-N-phenylacetamide (21)

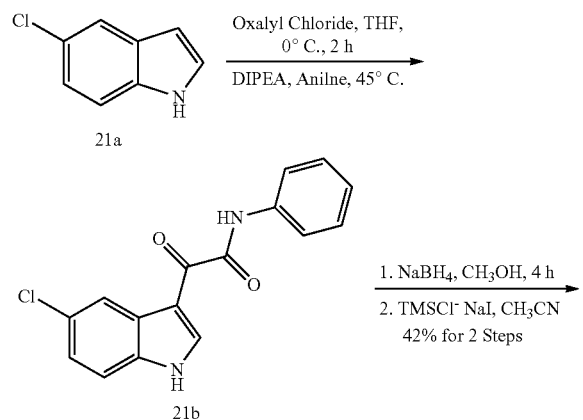

To a solution of 5-Chloro indole 21a (300 mg, 1.98 mmol) in anhydrous THF (20 mL), Oxalyl chloride (186 μL, 276 mg, 2.18 mmol) was added and the mixture stirred at room temperature. After 2 h, N,N-diisopropylethylamine (758 μL, 562 mg, 4.35 mmol) was introduced to the mixture, followed by the aniline (221.0 mg, 2.37 mmol). The temperature was raised to 45° C., and heating continued for 18 h. The solvent was evaporated, and then mixture was diluted with EtOAC (15 mL), washed with brine and dried over anhydrous $Na_2SO_4$. The crude material obtained after removal of solvent was purified by column chromatography (10-20% EtOAc:Petroleum ether) to afford (21b) (305 mg, 53% yield) as a yellow coloured solid. IR $\upsilon_{max}$ (film): 3346, 3307, 2853, 1724, 1678 cm$^{-1}$; $^1$H NMR (400 MHz, DMSO-$d_6$): δ 12.40 (br. s., 1H), 10.68 (s, 1H), 8.79 (d, J=3.2 Hz, 1H), 8.25 (d, J=8.6 Hz, 1H), 7.85 (d, J=7.8 Hz, 2H), 7.62 (d, J=1.7 Hz, 1H), 7.42-7.30 (m, 3H), 7.20-7.14 (m, 1H); $^{13}$C NMR (100 MHz, DMSO-$d_6$): δ 182.4, 162.4, 140.3, 138.4, 135.4, 129.2, 127.9, 124.8, 124.1, 120.8, 114.8, 112.0; HRMS (ESI) Calculated for $C_{16}H_{11}N_2OCl[M+H]^+$: 299.0582, found 299.0580; A solution of 21b (200 mg, 0.66 mmol) dissolved in MeOH (30 mL) was added to $NaBH_4$ (30 mg, 0.82 mmol). The reaction was stirred for 4 h and then added to saturated solution of $Na_2SO_4$. The reaction mixture was further stirred for 1 h and then filtered through Celite. The filtrate obtained was concentrated in vacuo, and then mixture was diluted with EtOAc (15 mL), washed with brine and dried over anhydrous $Na_2SO_4$. The crude material obtained after removal of solvent was forwarded for next step without further purification. In an $N_2$ atmosphere, TMSCl (848 mL, 6.6 mmol) in $CH_3CN$ (25 mL) was added to sodium iodide (992 mg, 6.6 mmol) and stirred for 2 h. The reaction mixture was cooled to 0° C. and a solution of above crude alcohol (0.66 mmol) in $CH_3CN$ (5 mL) was then added dropwise over 30 min, followed by stirring for 3 h. The reaction mixture was poured into NaOH (5 g in 30 mL of water) and then extracted with ethyl acetate (15×2). The organic layer was washed with aq.$Na_2S_2O_3$, dried over $Na_2SO_4$ and concentrated in vacuo. The residue was chromatographed on silica gel (EtOAc:Pet ether) to afford 22 as a off white solid (two steps 42%); IR $\upsilon_{max}$ (film): 3273, 3084, 2955, 2857, 1629, 1562 cm$^{-1}$; $^1$H NMR (400 MHz, DMSO-$d_6$): δ 11.13 (br. s., 1H), 10.11 (s, 1H), 7.67 (s, 1H), 7.60 (d, J=7.8 Hz, 2H), 7.39-7.27 (m, 4H), 7.13-7.02 (m, 2H), 3.16 (s, 2H); $^{13}$C NMR (100 MHz, DMSO-$d_6$): δ 169.9, 139.8, 135.0, 129.2, 128.9, 126.2, 123.6, 121.4, 119.6, 118.6, 113.4, 109.0, 34.0; HRMS (ESI) Calculated for $C_{16}H_{14}N_2OCl[M+H]^+$: 285.0789, found 285.0786.

Example 23

2-(1-benzyl-1H-indol-3-yl)-N-phenylacetamide (22)

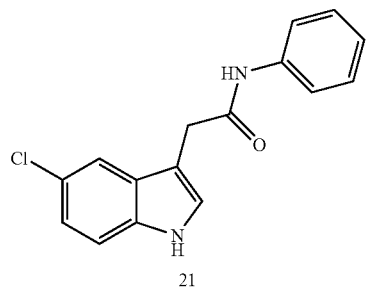

Yield 79%; $^1$H NMR (400 MHz, DMSO-$d_6$): δ 7.67 (d, J=7.8 Hz, 1H), 7.54 (brs, 1H), 7.43-7.31 (m, 6H), 7.31-7.25 (m, 3H), 7.23-7.15 (m, 4H), 7.12-7.06 (m, 1H), 5.36 (s, 2H), 3.91 (s, 2H); $^{13}$C NMR (100 MHz, DMSO-$d_6$): δ 169.7, 137.7, 137.2, 137.0, 128.9, 128.9, 127.9, 127.6, 126.9, 124.3, 122.7, 120.2, 119.9, 119.0, 110.2, 107.9, 77.4, 77.1, 76.8, 50.1, 34.5.

Example 24

Procedure B:

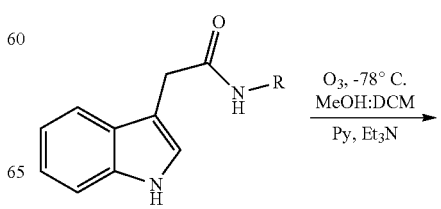

-continued

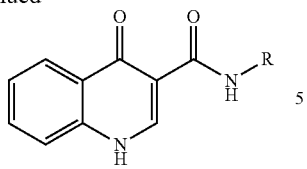

2-(1H-indol-3-yl)-N-phenylacetamide 1 (100 mg; 0.4 mmol) was dissolved in DCM:MeOH (50 mL; 5:1), then a stream of $O_3$ was passed through the solution until a blue color developed (10 min). The $O_3$ stream was continued for 4 min. Then surplus $O_3$ was removed by passing a stream of $O_2$ through the solution for 10 min or until the blue color completely vanished. Afterwards pyridine (0.1 mL; 1.2 mmol) was added to the cold (−78° C.) mixture. The mixture was allowed to warm to room temperature (1 h) and then $Et_3N$ (0.35 mL; 2.4 mmol) were added. After stirring at room temperature overnight the reaction mass was concentrated under reduced pressure to dryness, diluted with EtOAc (30 mL), washed with $H_2O$ (5 mL), brine (5 mL), and dried over $Na_2SO_4$. The crude material obtained after removal of solvent was purified by column chromatography (silica gel 230-400 mesh, MeOH-DCM) to give desired quinolone carboxamide as colorless solid.

Example 25

4-oxo-N-phenyl-1,4-dihydroquinoline-3-carboxamide (23)

Yield: 65 mg; 62%; $^1$H NMR (200 MHz, DMSO-$d_6$) δ=12.97 (brs, 1H), 12.49 (s, 1H), 8.89 (s, 1H), 8.33 (d, J=8.2 Hz, 1H), 7.91-7.69 (m, 4H), 7.62-7.50 (m, 1H), 7.37 (t, J=7.8 Hz, 2H), 7.18-7.01 (m, 1H); MS: 287 (M+Na)$^+$.

Example 26

2,4-di-tert-butyl-5-(4-oxo-1,4-dihydroquinoline-3-carboxamido)phenyl Methyl Carbonate (24)

Yield: 35 mg; 34%; $^1$H NMR (400 MHz, DMSO-$d_6$) δ=12.96 (brs, 1H), 12.08 (s, 1H), 8.94-8.82 (m, 1H), 8.44-8.28 (m, 1H), 7.86-7.79 (m, 1H), 7.78-7.73 (m, 1H), 7.59 (s, 1H), 7.53 (t, J=7.5 Hz, 1H), 7.39 (s, 1H), 3.86 (s, 3H), 1.46 (s, 9H), 1.32 (s, 9H).

Example 27

(S)-4-oxo-N-(1-phenylethyl)-1,4-dihydroquinoline-3-carboxamide (25)

Yield: 56 mg; 53%; $^1$H NMR (500 MHz, DMSO-$d_6$) δ=12.75 (brs, 1H), 10.54 (d, J=7.6 Hz, 1H), 8.73 (brs, 1H), 8.28 (d, J=7.9 Hz, 1H), 7.78 (d, J=7.9 Hz, 1H), 7.73-7.68 (m, 1H), 7.50 (t, J=7.5 Hz, 1H), 7.42-7.34 (m, 4H), 7.29-7.23 (m, 1H), 5.18 (t, J=7.2 Hz, 1H), 1.50 (d, J=6.7 Hz, 3H).

Example 28

Synthesis of Ivacaftor (26)

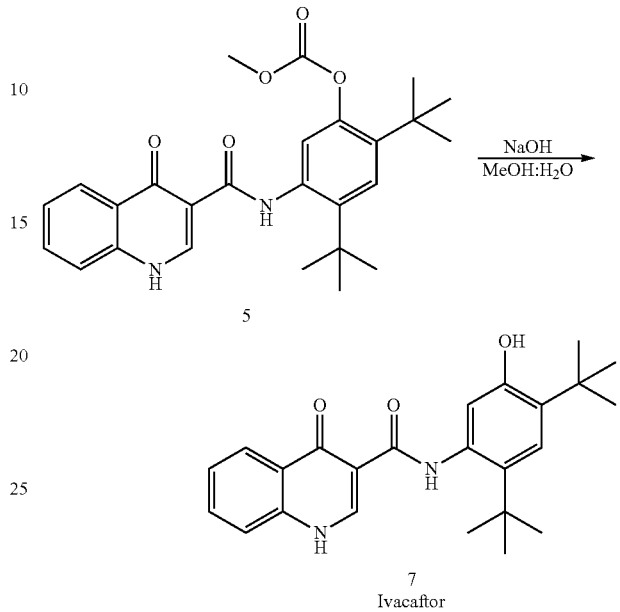

To a solution of 2,4-di-tert-butyl-5-(4-oxo-1,4-dihydroquinoline-3-carboxamido)phenyl methyl carbonate 5 (30 mg, 0.06 mmol) in MeOH (2 mL) was added NaOH (5.3 mg, 0.13 mmol) dissolved in $H_2O$ (2 mL), and the reaction mixture was stirred at room temperature for 5 h. Reaction mass was evaporated to one third of its volume (temperature not exceeding 40° C.) and acidified with aq.2N HCl to pH 2-3. The resulting precipitate was collected by suction filtration give desired compound 7 (19 mg, 76%) as off white solid. $^1$H NMR (400 MHz, DMSO-$d_6$) δ=12.88 (d, J=6.6 Hz, 1H), 11.81 (s, 1H), 9.20 (s, 1H), 8.86 (d, J=6.6 Hz, 1H), 8.32 (d, J=7.8 Hz, 1H), 7.88-7.65 (m, 2H), 7.51 (t, J=7.5 Hz, 1H), 7.16 (s, 1H), 7.10 (s, 1H), 1.38 (s, 9H), 1.36 (s, 9H).

Example 29

N-(4-fluorophenyl)-4-oxo-1,4-dihydroquinoline-3-carboxamide (27)

Yield 56%; $^1$H NMR (400 MHz, DMSO-$d_6$): δ 12.96 (br. s., 1H), 12.50 (s, 1H), 8.88 (s, 1H), 8.33 (d, J=7.3 Hz, 1H), 7.86-7.72 (m, 4H), 7.54 (t, J=7.3 Hz, 1H), 7.20 (t, J=8.8 Hz, 2H); $^{13}$C NMR (400 MHz, DMSO-$d_6$): δ 176.8, 163.2, 159.7, 157.3, 144.6, 139.6, 135.7, 133.5, 126.4, 125.9, 125.8, 121.8, 119.7, 116.1, 115.9, 110.9.

Example 30

N-(4-chlorophenyl)-4-oxo-1,4-dihydroquinoline-3-carboxamide (28)

Yield 51%; $^1$H NMR (400 MHz, DMSO-$d_6$): δ 13.00 (brs., 1H), 12.59 (br. s., 1H), 8.89 (s, 1H), 8.34 (d, J=7.6 Hz, 1H), 7.83-7.76 (m, 4H), 7.56 (s, 1H), 7.42 (d, J=7.9 Hz, 2H); $^{13}$C NMR (400 MHz, DMSO-d$_6$): δ 176.8, 163.4, 144.7, 139.6, 138.2, 133.5, 129.4, 127.4, 126.4, 125.9, 125.8, 121.6, 119.7, 110.8.

Example 31

4-oxo-N-(p-tolyl)-1,4-dihydroquinoline-3-carboxamide (29)

Yield 57%; $^1$H NMR (400 MHz, DMSO-d$_6$): δ 12.94 (brs., 1H), 12.40 (s, 1H), 8.88 (s, 1H), 8.33 (d, J=7.8 Hz, 1H), 7.82-7.80 (m, 1H), 7.76-7.7 (m, 1H), 7.63 (d, J=8.3 Hz, 2H), 7.53 (t, J=7.3 Hz, 1H), 7.17 (d, J=8.1 Hz, 2H), 2.29 (s, 3H); $^{13}$C NMR (100 MHz, DMSO-d$_6$): δ 176.8, 163.1, 144.5, 139.6, 136.8, 133.4, 132.8, 129.9, 126.4, 125.9, 125.7, 120.0, 119.6, 111.1, 20.9; HRMS (ESI): Calculated for C$_{17}$H$_{15}$O$_2$N$_2$[M+H]$^+$: 279.1128, found 279.1127.

Example 32

N-(4-ethylphenyl)-4-oxo-1,4-dihydroquinoline-3-carboxamide (30)

Yield 51%; $^1$H NMR (400 MHz, DMSO-d$_6$): δ 12.95 (br. s., 1H), 12.40 (d, J=7.8 Hz, 1H), 8.87 (d, J=6.1 Hz, 1H), 8.33 (d, J=8.1 Hz, 1H), 7.81-7.76 (m, 2H), 7.66-7.62 (m, J=8.3 Hz, 2H), 7.53 (t, J=7.5 Hz, 1H), 7.22-7.17 (m, J=8.3 Hz, 2H), 2.58 (q, J=7.6 Hz, 2H), 1.18 (t, J=7.6 Hz, 3H); $^{13}$C NMR (400 MHz, DMSO-d$_6$): δ 181.5, 167.8, 149.3, 144.3, 144.0, 141.7, 138.2, 133.4, 131.1, 130.7, 130.5, 124.8, 124.4, 115.9, 32.8, 20.9.

Example 33

4-Oxo-N-(4-propylphenyl)-1,4-dihydroquinoline-3-carboxamide (31)

Yield 51%; $^1$H NMR (500 MHz, DMSO-d6): δ12.93 (brs, 1H), 12.40 (s, 1H), 8.87 (s, 1H), 8.36-8.29 (m, 1H), 7.86-7.78 (m, 1H), 7.75 (d, J=7.9 Hz, 1H), 7.68-7.61 (m, J=8.2 Hz, 2H), 7.54 (t, J=7.6 Hz, 1H), 7.22-7.14 (m, J=8.2 Hz, 2H), 2.55-2.51 (m, 2H), 1.64-1.53 (m, 2H), 0.90 (t, J=7.3 Hz, 3H); $^{13}$C NMR (500 MHz, DMSO-d6): 176.8, 163.1, 144.5, 139.6, 137.6, 137.0, 133.5, 129.3, 126.4, 125.9, 125.7, 120.0, 119.7, 111.1, 37.2, 24.6, 14.1.

Example 34

N-(4-isopropylphenyl)-4-oxo-1,4-dihydroquinoline-3-carboxamide (32)

Yield 46%; $^1$H NMR (500 MHz, DMSO-d$_6$): δ 12.93 (br. s., 1H), 12.40 (br. s., 1H), 8.89-8.86 (m, 1H), 8.33 (d, J=7.6 Hz, 1H), 7.81-7.50 (m, 5H), 7.25-7.21 (m, 2H), 2.90-2.83 (m, 1H), 1.22-1.11 (m, 6H); $^{13}$C NMR (100 MHz, DMSO-d$_6$): δ 176.8, 163.1, 144.5, 143.9, 139.6, 137.1, 133.4, 127.2, 126.4, 125.9, 125.7, 120.1, 119.6, 111.1, 33.4, 24.4.

Example 35

4-oxo-N-(4-(trifluoromethoxy)phenyl)-1,4-dihydroquinoline-3-carboxamide (33)

Yield 57%; $^1$H NMR (400 MHz, DMSO-d$_6$): δ 12.98 (br. s., 1H), 12.63 (s, 1H), 8.88 (d, J=4.9 Hz, 1H), 8.32 (d, J=7.8 Hz, 1H), 7.89-7.83 (m, J=8.8 Hz, 2H), 7.79 (d, J=7.6 Hz, 1H), 7.77-7.73 (m, 1H), 7.53 (t, J=7.5 Hz, 1H), 7.40-7.34 (m, J=8.6 Hz, 2H); $^{13}$C NMR (100 MHz, DMSO-d$_6$): δ 176.8, 163.5, 144.7, 144.0, 139.5, 138.5, 133.5, 126.3, 125.9, 125.8, 122.3, 121.4, 119.7, 110.7.

Example 36

N-(2-chloro-5-methoxyphenyl)-4-oxo-1,4-dihydroquinoline-3-carboxamide (34)

Yield 54%; $^1$H NMR (400 MHz, DMSO-d$_6$): δ 12.98 (br. s., 1H), 12.49 (s, 1H), 8.88 (s, 1H), 8.33 (d, J=7.8 Hz, 1H), 7.83-7.75 (m, 1H), 7.56-7.48 (m, 3H), 7.27-7.21 (m, 1H), 6.67 (d, J=7.8 Hz, 1H), 3.77 (s, 3H); $^{13}$C NMR (400 MHz, DMSO-d$_6$): δ 176.8, 163.4, 160.2, 144.7, 140.4, 139.6, 133.5, 130.3, 126.4, 125.9, 125.8, 119.7, 112.3, 111.0, 109.5, 105.7, 55.5.

Example 37

N-(2-ethylphenyl)-4-oxo-1,4-dihydroquinoline-3-carboxamide (35)

Yield 58%; $^1$H NMR (400 MHz, DMSO-d$_6$): δ 12.94 (br. s., 1H), 12.37 (s, 1H), 8.90 (s, 1H), 8.36 (dd, J=8.1, 1.4 Hz, 2H), 8.32 (dd, J=8.1, 1.4 Hz, 2H), 7.82-7.74 (m, 1H), 7.53-7.19 (m, 3H), 7.15-7.06 (m, 1H), 2.79 (q, J=7.3 Hz, 2H), 1.26 (t, J=7.5 Hz, 3H); 293 (M+H)$^+$.

Example 38

N-(2-bromophenyl)-4-oxo-1,4-dihydroquinoline-3-carboxamide (36)

Yield 47%; $^1$H NMR (200 MHz, DMSO-d$_6$): δ 12.98 (br. s., 1H), 12.69 (s, 1H), 8.90 (d, J=5.9 Hz, 1H), 8.54 (dd, J=1.4, 8.3 Hz, 1H), 8.34 (d, J=7.6 Hz, 1H), 7.86-7.67 (m, 3H), 7.57-7.49 (m, 1H), 7.40 (t, J=7.2 Hz, 1H), 7.10-7.05 (m, 1H); $^{13}$C NMR (100 MHz, DMSO-d$_6$): δ 176.7, 163.7, 145.0, 139.5, 137.7, 133.5, 133.1, 128.6, 126.4, 126.0, 125.8, 125.3, 122.9, 119.7, 113.4, 110.8.

Example 39

N-benzyl-4-oxo-1,4-dihydroquinoline-3-carboxamide (37)

Yield 58%; $^1$H NMR (400 MHz, CD$_3$OD-d$_6$): δ 8.82 (s, 1H), 8.35 (d, J=8.1 Hz, 1H), 7.79-7.77 (m, 1H), 7.65 (d, J=8.3 Hz, 1H), 7.52 (t, J=7.6 Hz, 1H), 7.42-7.34 (m, 4H), 7.31-7.26 (m, 1H), 4.67 (s, 2H); $^{13}$C NMR (400 MHz, DMSO-d$_6$): δ 176.6, 165.0, 144.2, 140.0, 139.5, 133.2, 128.9, 128.7, 127.8, 127.3, 126.6, 125.9, 125.4, 119.5, 111.2, 42.6.

Example 40

N-(4-methoxybenzyl)-4-oxo-1,4-dihydroquinoline-3-carboxamide (38)

Yield 56%; $^1$H NMR (400 MHz, DMSO-d$_6$): δ 12.73 (br. s., 1H), 10.35 (t, J=5.3 Hz, 1H), 8.78 (d, J=6.1 Hz, 1H), 8.24 (d, J=8.1 Hz, 1H), 7.76 (d, J=7.1 Hz, 1H), 7.73-7.68 (m, 1H), 7.48 (t, J=7.5 Hz, 1H), 7.28 (d, J=8.3 Hz, 2H), 6.91 (d, J=8.1 Hz, 2H), 4.49 (d, J=5.6 Hz, 2H), 3.74 (s, 3H); $^{13}$C NMR (100 MHz, DMSO-d$_6$): δ 176.6, 164.8, 158.8, 144.1, 139.5, 133.1, 131.9, 129.2, 126.6, 125.8, 125.4, 119.5, 114.3, 111.3, 55.5, 42.0.

Example 41

N,N-dibenzyl-4-oxo-1,4-dihydroquinoline-3-carboxamide (39)

Yield 43%; $^1$H NMR (400 MHz, DMSO-d$_6$): δ 12.21 (br. s., 1H), 8.27 (d, J=4.9 Hz, 1H), 8.21 (d, J=7.6 Hz, 1H), 7.49-7.41 (m, 2H), 7.41-7.35 (m, 3H), 7.33-7.20 (m, 5H), 7.20-7.11 (m, J=7.1 Hz, 2H), 4.59 (br. s., 2H), 4.42 (s, 2H).

Example 42

4-oxo-N-propyl-1,4-dihydroquinoline-3-carboxamide (40)

Yield 47%; $^1$H NMR (400 MHz, DMSO-d$_6$): δ 12.7 (br.s., 1H) 10.05 (t, J=5.5 Hz, 1H), 8.74 (s, 1H), 8.26 (d, J=8.1 Hz, 1H), 7.83-7.66 (m, 2H), 7.52-7.44 (m, 1H), 3.33-3.22 (m, 2H), 1.61-1.49 (m, 2H), 0.93 (t, J=7.5 Hz, 3H); $^{13}$C NMR (100 MHz, DMSO-d$_6$): δ 176.6, 164.8, 143.9, 139.5, 133.1, 126.6, 125.9, 125.3, 119.4, 111.4, 39.3, 23.1, 12.0

Example 43

N-hexyl-4-oxo-1,4-dihydroquinoline-3-carboxamide (41)

Yield 51%; $^1$H NMR (400 MHz, DMSO-d$_6$): δ 12.68 (m, 1H), 10.02 (t, J=5.5 Hz, 1H), 8.73 (d, J=6.1 Hz, 1H), 8.27-8.25 (m, 1H), 7.77-7.67 (m, 2H), 7.47 (t, J=7.5 Hz, 1H), 3.33-3.29 (m, 2H), 1.56-1.45 (m, 2H), 1.34-1.25 (m, 6H), 0.88-0.82 (m, 3H); $^{13}$C NMR (100 MHz, DMSO-d$_6$): δ 176.6, 164.8, 143.9, 139.5, 133.1, 126.6, 125.9, 125.3, 119.4, 111.4, 38.7, 31.5, 29.8, 26.7, 22.5, 14.4.

Example 44

Methyl (4-oxo-1,4-dihydroquinoline-3-carbonyl)-L-alaninate (42)

Yield 38%; $^1$H NMR (400 MHz, CD$_3$OD): δ 8.74 (s, 1H), 8.47-8.29 (m, 1H), 7.86-7.76 (m, 1H), 7.64 (d, J=8.3 Hz, 1H), 7.58-7.44 (m, 1H), 4.69 (d, J=7.3 Hz, 1H), 3.79 (s, 3H), 1.55 (d, J=7.3 Hz, 3H); $^{13}$C NMR (100 MHz, CD$_3$OD): δ 177.3, 173.3, 165.5, 143.6, 139.2, 132.9, 126.3, 125.4, 125.2, 118.5, 110.3, 51.5, 47.0, 17.0.

Example 45

7-chloro-4-oxo-N-phenyl-1,4-dihydroquinoline-3-carboxamide (43)

Yield 48%; IR υ$_{max}$ (film): 2920, 2868, 1661, 1601 cm$^{-1}$; $^1$H NMR (400 MHz, DMSO-d$_6$): δ 12.91 (br. s., 1H), 12.30 (s, 1H), 8.90 (s, 1H), 8.29 (d, J=8.8 Hz, 1H), 7.80-7.67 (m, 3H), 7.58-7.51 (m, 1H), 7.36 (t, J=7.7 Hz, 2H), 7.09 (t, J=7.3 Hz, 1H); $^{13}$C NMR (100 MHz, DMSO-d$_6$): δ 176.3, 162.9, 145.4, 140.3, 139.2, 138.0, 129.5, 128.2, 126.1, 125.1, 123.9, 120.1, 118.8, 111.6.

Example 46

6-chloro-4-oxo-N-phenyl-1,4-dihydroquinoline-3-carboxamide (44)

Yield 52%; $^1$H NMR (400 MHz, DMSO-d$_6$): δ 13.05 (brs, 1H), 12.27 (s, 1H), 8.88 (s, 1H), 8.21 (d, J=2.2 Hz, 1H), 7.86-7.67 (m, 4H), 7.36 (t, J=7.8 Hz, 2H), 7.16-7.04 (m, 1H); $^{13}$C NMR (100 MHz, DMSO-d$_6$): δ 175.6, 162.9, 144.9, 139.1, 138.2, 133.5, 130.4, 129.5, 127.5, 124.9, 123.9, 122.0, 120.1, 111.4.

Example 47

1-benzyl-4-oxo-N-phenyl-1,4-dihydroquinoline-3-carboxamide (45)

Yield 55%; $^1$H NMR (400 MHz, DMSO-d$_6$): δ 12.30 (s, 1H), 9.05 (s, 1H), 8.60 (dd, J=1.7, 8.1 Hz, 1H), 7.82 (d, J=7.8 Hz, 2H), 7.69-7.62 (m, 1H), 7.55-7.45 (m, 2H), 7.43-7.34 (m, 5H), 7.24-7.18 (m, 2H), 7.17-7.10 (m, 1H), 5.53 (s, 2H); $^{13}$C NMR (100 MHz, DMSO-d$_6$): δ 176.9, 162.9, 148.7, 139.3, 138.7, 134.1, 133.1, 129.4, 128.9, 128.7, 128.0, 127.4, 126.2, 125.5, 123.9, 120.5, 116.9, 112.3, 57.9; HRMS (ESI): Calculated for C$_{23}$H$_{18}$O$_2$N$_2$Na [M+Na]$^+$: 377.1260, found 377.1259; MS: 355 (M+H)$^+$.

Advantages of Invention:
1. Cost-effective process for synthesis.
2. Carried out at environmentally benign conditions.
3. Short synthetic route.
4. Useful for making several related compounds of medicinal use.

We claim:
1. A one pot process for the preparation of compounds of formula (I) and formula (II);

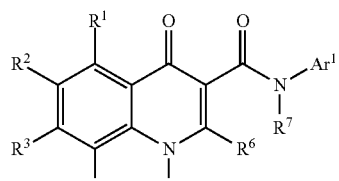

Formula (I)

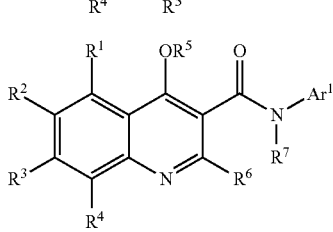

Formula (II)

wherein, Ar$^1$ is a 5-6 membered aromatic/hetero aromatic ring, which could be further substituted by alkyl, aryl, hetero aryl and having 0-4 heteroatoms independently selected from nitrogen, oxygen, or sulfur, wherein said ring is optionally fused to a 5-12 membered monocyclic or bicyclic, aromatic, partially unsaturated, or saturated ring, wherein each ring contains 0-4 heteroatoms independently selected from nitrogen, oxygen, or sulfur, wherein Ar$^1$ has m substituents, each selected independently from —WR$^W$; W is a bond or is an optionally substituted C$_1$-C$_6$ alkylidene chain wherein up to two methylene units of W are optionally and independently replaced by —CO—, —CS—, —COCO—, —CONR'—, —CONR'NR'—, —CO$_2$—, —OCO—, —NR'CO$_2$—, —O—, —NR'CONR'—, OCONR', —NRTSIR', —NR'NR'CO—, —NR'CO—, —S—, —SO, —SO$_2$—, —NR'—, —SO$_2$NR'—, NR'SO$_2$, or —NR'SO$_2$NR'—; R$^W$ is independently R', halo, NO$_2$, CN, CF$_3$, or OCF$_3$; m is 0-5; each of R$^1$, R$^2$, R$^3$, R$^4$, and R$^5$ is hydrogen, —X—R$^X$; X is a bond or is an optionally substituted $C_1$-$C_6$ alkylidene chain wherein up to two methylene units of X are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NRTSIR', —NR'N-R'CO—, —NR'CO—, —S—, —SO, —$SO_2$—, —NR'—, —$SO_2$NR'—, NR'$SO_2$—, or —NR'$SO_2$NR'—; $R^X$ is independently R', halo, $NO_2$, CN, $CF_3$, or $OCF_3$; $R^6$ is hydrogen, $CF_3$, —OR', —SR', or an optionally substituted $C_{1-6}$ aliphatic group; $R^7$, $R^8$ is hydrogen or a $C_{1-6}$ aliphatic group optionally substituted with —X—$R^X$; R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; its tautomers or pharmaceutically acceptable salts thereof comprising the steps of;
  a) coupling indole acetic acid with corresponding amines using suitable coupling agent to obtain indole amides;
  b) oxidizing indole amides of step (a) using suitable oxidizing agent followed by treatment with base to obtain desired quinolone carboxamides with 40 to 65% yield, wherein the base is an organic base selected from pyridine, 2,6-lutidine, DMAP (4-dimethylaminopyridine), $Et_3N$ (triethylamine), DIPEA (N,N-diisopropyl ethyl amine), N,N-dimethylaniline, DBN (1,5-diazabicyclo(4.3.0)non-5-ene), DABCO (1,4-diazabicyclo[2.2.2]octane) and DBU (1,8-diazabicycloundec-7-ene) or mixture thereof.

2. The process as claimed in claim 1, wherein the quinolone carboxamide compound is selected from 4-oxo-N-phenyl-1,4-dihydroquinoline-3-carboxamide (23), 2,4-di-tert-butyl-5-(4-oxo-1,4-dihydroquinoline-3-carboxamido) phenyl methyl carbonate (24), N-(4-fluorophenyl)-4-oxo-1,4-dihydroquinoline-3-carboxamide (27), N-(4-chlorophenyl)-4-oxo-1,4 dihydroquinoline-3-carboxamide (28), 4-oxo-N-(p-tolyl)-1,4-dihydroquinoline-3-carboxamide (29), N-(4-ethylphenyl)-4-oxo-1,4-dihydroquinoline-5 3-carboxamide (30), 4-Oxo-N-(4-propylphenyl)-1,4-dihydroquinoline-3-carboxamide (31), N-(4-isopropylphenyl)-4-oxo-1,4-dihydroquinoline-3-carboxamide (32), 4-oxo-N-(4-(trifluoromethoxy)phenyl)-1,4-dihydroquinoline-3-carboxamide (33), N-(2-chloro-5-methoxyphenyl)-4-oxo-1,4-dihydroquinoline-3-carboxamide (34), N-(2-ethylphenyl)-4-oxo-1,4-dihydroquinoline-3-carboxamide (35), N-(2-bromophenyl)-4-oxo-1,4-dihydroquinoline-3-carboxamide (36), 7-chloro-4-oxo-N-phenyl-1,4-dihydroquinoline-3-carboxamide (43), 6-chloro-4-oxo-N-phenyl-1,4-dihydroquinoline-3-carboxamide (44), 1-benzyl-4-oxo-N-phenyl-1,4-dihydroquinoline-3-carboxamide (45).

3. The process as claimed in claim 1, wherein the indole amides is selected from 2-(1H-indol-3-yl)-N-phenylacetamide (1), 5-(2-(H-indol-3-yl)acetamido)-2,4-di-tert-butylphenyl methyl carbonate (2), N-(4-Fluorophenyl)-2-(1H-indol-3-yl)acetamide (4), N-(4-Chlorophenyl)-2-(1H-indol-3-yl)acetamide (5), 2-(1H-indol-3-yl)-N-(p-tolyl)acetamide (6), N-(4-Ethylphenyl)-2-(1H-indol-3-yl)acetamide (7), 2-(1H-Indol-3-yl)-N-(4-propylphenyl)acetamide (8), 2-(1H-Indol-3-yl)-N-(4-isopropylphenyl)acetamide (9), 2-(1H-indol-3-yl)-N-(4-(trifluoromethoxy)phenyl)acetamide (10), N-(2-chloro-5-methoxyphenyl)-2-(1H-indol-3-yl)acetamide (11), N-(2-ethylphenyl)-2-(1H-indol-3-yl)acetamide (12), N-(2-bromophenyl)-2-(1H-indol-3-yl)acetamide (13), 2-(6-chloro-1H-indol-3-yl)-N-phenylacetamide (20), (5-chloro-1H-indol-3-yl)-N-phenylacetamide (21), 2-(1-benzyl-1H-indol-3-yl)-N-5 phenyl acetamide (22).

4. The process as claimed in claim 1, wherein the corresponding amines in step (a) is selected from compounds of Formula $Ar_1$—NH—$R^7$, wherein $Ar^1$ is a 5-6 membered aromatic/hetero aromatic ring, which could be further substituted by alkyl, aryl, hetero aryl and having 0-4 heteroatoms independently selected from nitrogen, oxygen, or sulfur, wherein said ring is optionally fused to a 5-12 membered monocyclic or bicyclic, aromatic, partially unsaturated, or saturated ring, wherein each ring contains 0-4 heteroatoms independently selected from nitrogen, oxygen, or sulfur, wherein $Ar^1$ has m substituents, each independently selected from —$WR^W$; W is a bond or is an optionally substituted $C_1$-$C_6$ alkylidene chain wherein up to two methylene units of W are optionally and independently replaced by —CO—, —CS—, —COCO—, —CONR'—, —CONR'NR'—, —$CO_2$—, —OCO—, —NR'$CO_2$—, —O—, —NR'CONR'—, —OCONR'—, —NR NR', —NR'N-R'CO—, —NR'CO—, —S—, —SO, —$SO_2$—, —NR'—, —$SO_2$NR'—, NR'$SO_2$—, or —NR'$SO_2$NR'—; $R^W$ is independently R', halo, $NO_2$, CN, $CF_3$, or $OCF_3$; m is 0-5; $R^7$, $R^8$ is hydrogen or a $C_{1-6}$ aliphatic group optionally substituted with —X—$R^X$; and $R^X$ is independently R', halo, $NO_2$, CN, $CF_3$, or $OCF_3$.

5. The process as claimed in claim 1, wherein the coupling agent in step (a) is selected from HATU (1-[bis(dimethylamino)methylene]-1H-1,2,3-triazolo[4,5-b]pyridinium 3-oxid hexafluoro phosphate) or HBTU (O-benzotriazole-N,N,N',N'-tetramethyl-uronium-hexafluoro-phosphate), hydroxybenzotriazole or (EDC) 1-ethyl-3-(3-25 dimethylaminopropyl)carbodiimide or DCC (N,N'-dicyclohexylcarbodiimide), or DIC (N,N'-diisopropylcarbodiimide) or CDI (1,1'-carbonyldiimidazole) or TBTU (O-(benzotriazol-1-yl)-N,N',N'-tetramethyluroniumtetrafluoroborate) or FDPP (pentafluorophenyldiphenylphosphinate).

6. The process as claimed in claim 1, wherein the coupling agent is carbodiimides.

7. The process as claimed in claim 1, wherein the oxidizing agent in step (b) is selected from sodium periodate, peroxides, potassium permanganate, $CrO_3$, or ozone.

8. The process as claimed in claim 1, wherein the oxidizing agent in step (b) is ozone.

9. The process as claimed in claim 1, wherein the base is pyridine or triethylamine.

10. The process as claimed in claim 1, wherein said process is a one pot process for the synthesis of compounds of Formula (I), its tautomers or pharmaceutically acceptable salts thereof comprising the steps of:
  a) adding EDC.HCl and DIPEA to a solution of indole acetic acid, aniline and HOBt in acetonitrile followed by stirring the reaction mixture for 16 h at room temperature to obtain indole amides;
  b) passing a stream of $O_3$ to a solution of compound of step (a) in DCM:MeOH and adding pyridine and triethylamine followed by stirring the reaction mixture for overnight at room temperature to obtain desired compounds.

11. The process as claimed in claim 1, wherein said process further comprising:
  deprotection of phenol in the quinolone carboxamides of step (b) under basic condition to afford ivacaftor.

12. The process as claimed in claim 10, wherein said process further comprising:
   addition of NaOH dissolved in $H_2O$ to a solution of compound of step (b) in methanol followed by stirring the reaction mixture for 5 h at room temperature to obtain ivacaftor.

\* \* \* \* \*